(12) United States Patent
Soo

(10) Patent No.: US 10,016,452 B2
(45) Date of Patent: Jul. 10, 2018

(54) FIBROMODULIN FORMULATION FOR REDUCING CORNEAL SCARRING

(75) Inventor: Chia Soo, Beverly Hills, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 753 days.

(21) Appl. No.: 12/937,324

(22) PCT Filed: May 1, 2009

(86) PCT No.: PCT/US2009/042536
§ 371 (c)(1),
(2), (4) Date: Dec. 16, 2010

(87) PCT Pub. No.: WO2009/135135
PCT Pub. Date: Nov. 5, 2009

(65) Prior Publication Data
US 2011/0086807 A1    Apr. 14, 2011

Related U.S. Application Data

(60) Provisional application No. 61/049,677, filed on May 1, 2008.

(51) Int. Cl.
| | | |
|---|---|---|
| *A61K 31/728* | (2006.01) | |
| *A61K 38/17* | (2006.01) | |
| *A61K 45/06* | (2006.01) | |
| *A61K 9/00* | (2006.01) | |

(52) U.S. Cl.
CPC .......... *A61K 31/728* (2013.01); *A61K 9/0048* (2013.01); *A61K 38/1709* (2013.01); *A61K 45/06* (2013.01)

(58) Field of Classification Search
None
See application file for complete search history.

(56) References Cited

U.S. PATENT DOCUMENTS

| | | |
|---|---|---|
| 3,755,560 A | 8/1973 | Dickert et al. |
| 4,421,769 A | 12/1983 | Dixon et al. |
| 4,648,400 A | 3/1987 | Schneider et al. |
| 4,665,913 A | 5/1987 | L'Esperance, Jr. |
| 4,669,466 A | 6/1987 | L'Esperance |
| 4,732,148 A | 3/1988 | L'Esperance, Jr. |
| 4,770,172 A | 9/1988 | L'Esperance, Jr. |
| 4,773,414 A | 9/1988 | L'Esperance, Jr. |
| 4,973,493 A | 11/1990 | Guire |
| 5,163,903 A | 11/1992 | Crittenden et al. |
| 5,192,535 A | 3/1993 | Davis et al. |
| 5,382,243 A | 1/1995 | Mulholland |
| 5,467,147 A | 11/1995 | Faranda |
| 2002/0010130 A1* | 1/2002 | Beaulieu .............. A61K 9/0014 514/9.3 |
| 2002/0115589 A1 | 8/2002 | Nixon et al. |
| 2003/0032591 A1* | 2/2003 | Ruoslahti et al. .............. 514/12 |

FOREIGN PATENT DOCUMENTS

| | | |
|---|---|---|
| WO | WO 1993/009800 | 5/1993 |
| WO | WO 1993/019783 | 10/1993 |
| WO | WO 2009/135135 | 11/2009 |

OTHER PUBLICATIONS

"Patient." Merriam-Webster.com. Merriam-Webster, n.d. Web. Oct. 4, 2017; p. 1 (Year: 2017).*
"Individual." Merriam-Webster.com. Merriam-Webster, n.d. Web. Oct. 4, 2017; p. 1 (Year: 2017).*
"Lozenge." Merriam-Webster.com. Merriam-Webster, n.d. Web. Oct. 4, 2017; p. 1 (Year: 2017).*
Stoff et al., "Effect of adenoviral mediated overexpression of fibromodulin on human dermal fibroblasts and scar formation in full-thickness incisional wounds", J. Mol. Med. vol. 85, pp. 481-496 Abstract only (2007).
International Search Report for International Application No. PCT/US2009/042536, dated Nov. 30, 2009.
Written Opinion of the International Searching Authority for International Application No. PCT/US2009/042536, dated Nov. 30, 2009.
International Preliminary Report on Patentability International Application No. PCT/US2009/042536, dated Nov. 2, 2010.

* cited by examiner

*Primary Examiner* — Lianko G Garyu
(74) *Attorney, Agent, or Firm* — Duane Morris LLP

(57) ABSTRACT

A formulation for reducing corneal scarring and related eye conditions, is disclosed. The formulation comprises an effective amount of fibromodulin and can be administered intraocularly, such as by topical application, injection into the eye, or implantation in or on the eye.

20 Claims, No Drawings

FIBROMODULIN FORMULATION FOR REDUCING CORNEAL SCARRING

FIELD OF THE INVENTION

The invention is directed to a composition for reducing scarring in a corneal tissue.

BACKGROUND

The human eye is an extremely powerful focusing device that produces an image on the surface of the retina. The focusing elements of the eye are the cornea and the lens. The cornea accounts for approximately 80 percent of the focusing ability (48 diopters) and the lens approximately 20 percent (12 diopters). In the case of myopia, the eye is assumed to have a longer egg-like shape in which case the light beam focuses to a spot located in front of the retina and therefore is out of focus. In hyperopia, the focusing system is inadequate, and the focusing spot and image are located behind the retina and also out of focus. In the case of astigmatism, a spot or clear image is not created, and the eye basically focuses at two areas behind or in front of the retinal surface. In order to correct myopia, hyperopia, or astigmatism, spectacles or contact lenses are used to place the image directly on the rods and cones of the retina.

The cornea is a thin shell with nearly concentric anterior and posterior surfaces and a central thickness of about 520 micrometers. It has an index of refraction of 1.377 and a nominal radius of curvature of 7.86 mm. The epithelium, forming the anterior surface of the cornea, is about 50 micrometers thick. The epithelial cells are capable of very rapid regrowth, and it is known that the epithelium can be removed from the cornea and will quickly regrow to resurface the area from which it was removed. Underlying the epithelium is a layer called Bowman's layer or Bowman's membrane, which is about 20 micrometers thick. This covers the anterior surface of the stroma, which makes up the bulk of the cornea and consists primarily of collagen fibers. The endothelium, forming the posterior layer of the cornea, is a single layer of cells that do not reproduce.

Damage to the corneal epithelium, such as by abrasion or other trauma, is quickly repaired (usually within 24-48 hours) by growth of the rapidly dividing epithelial cells. However, this rapid proliferation of corneal epithelial cells can frequently lead to the development of scar tissue. The presence of scar tissue in the cornea results in 'corneal haze'—an opacification of the cornea in which vision is dramatically reduced due to the inability of light to pass through the cornea. Treatment of corneal opacification varies with the extent of scar tissue formation. In cases where the scarring remains light and affects only the surface of the cornea, surgery or laser removal is the treatment of choice. In situations where the scar tissue extends deeper into the cornea removal of the entire tissue and transplantation of a new cornea is the recommended treatment. Prevention of scarring in this tissue after injury is thus a critical step in the preservation of vision.

A number of corneal injuries are known to typically produce scarring of the cornea. These fall into three broad categories: trauma, infection, and disease conditions. Natural traumas (such as abrasion or chemical burns), as well as trauma associated with medical correction of vision (such as photoablation, or contact lens-induced injury) cause disruption of the normal corneal epithelium, resulting in rapid growth of these cells and formation of scar tissue. Damage to the cornea resulting from surgery, such as transplantation, also commonly leads to scarring of this tissue.

Infections of the eye by bacteria, viruses, or fungi can also lead to scarring. For example, ocular infection by herpes simplex virus type I, *Pneumococcus, Staphylococcus, Escherichia coli, Proteus, Klebsiella* and *Pseudomonas* strains are known to cause ulcer formation on the surface of the cornea. Such ulcers not only destroy the surrounding epithelial layer, but also penetrate and damage the corneal stroma, further aided by acute inflammatory cells and collagenase released by the injured epithelial cells themselves. Such deep and extensive damage to the cornea and surrounding tissues results in extensive scarring. Other, non-ulcerative pathogens are also known to lead to scarring of the cornea. One such organism is herpes zoster virus (shingles); infection by this organism causes abrasions to the corneal epithelium which frequently result in scarring.

A number of disease conditions not immediately caused by a pathogen or trauma have also been implicated in corneal opacification due to scarring. Two such conditions are cicatricial pemphigoid and Stevens-Johnson syndrome (SJS). Cicatricial pemphigoid is an autoimmune blistering disease affecting oral mucosa and the conjunctiva of the eye, in which inflammation of the corneal epithelium leads to scarring. SJS is a severe form of erythema multiforme, an immune complex-mediated hypersensitivity reaction. The ocular manifestation of this disease is ulceration of the epithelium, followed by severe scarring.

While treatments exist for each of the specific injuries enumerated above, there does not exist in the art a reliable method for reducing or eliminating scarring after corneal injury such that corneal opacification is prevented. The study of corrective vision treatments by photoablation has provided a model system for examining the scarring response and treatments devoted thereto in corneal tissue.

Laser photoablation of corneal tissue can be utilized to correct refractive errors in the eye. About three-quarters of the refractive power of the eye is determined by the curvature of the anterior surface of the cornea, so that changing the shape of the cornea offers a way to significantly reduce or eliminate a refractive error of the eye. Since the epithelium readily regrows, a change in the shape of the anterior surface of the cornea must be made by modifying Bowman's layer and the stroma to be permanent. The stroma is thick enough so that portions of its anterior region can be ablated away to change its profile and thus change the refractive power of the eye for corrective purposes, while leaving plenty of remaining stroma tissue. For example, a change of 5 diopters requires only 27 µm of stromal removal within a 4 mm diameter region.

As discovered by Stephen L. Trokel ("Excimer laser Surgery of the Cornea", American Journal of Ophthalmology, December 1983), far ultraviolet radiation from an excimer laser can be used to change the refractive power of the cornea of an eye. The radiation ablates away corneal tissue in a photodecomposition that does not cause thermal damage to adjacent tissue and can be called photorefractive keratectomy (PRK). A similar photodecomposition of corneal tissue can be achieved with an infrared laser operating near 2.9 micrometers, where thermal damage to adjacent tissue is minimized by the high absorption of water.

L'Esperance U.S. Pat. No. 4,665,913 describes procedures for changing the contour of the anterior surface of the cornea of the eye by directing pulses from an excimer laser in a scanning pattern that moves around the cornea. The laser pulses first ablate and remove the epithelium of the cornea, and then the ablation penetrates into the stroma of the cornea to change its contour for various purposes, such as correcting myopia or hyperopia. Schneider et al. U.S. Pat. No. 4,648,400 suggests radial keratectomy with an excimer laser that also ablates away the epithelium before penetrating into and changing the contour of, the stroma of the cornea.

Ultraviolet laser based systems and methods which are known for enabling ophthalmological surgery on the surface of the cornea in order to correct vision defects by the technique known as ablative photodecomposition. In such systems and methods, the irradiated flux density and exposure time of the cornea to the ultraviolet laser radiation are so controlled as to provide a surface sculpting of the cornea to achieve a desired ultimate surface change in the cornea, all in order to correct an optical defect. Such systems and methods are disclosed in the following U.S. patents and patent applications, the disclosures of which are hereby incorporated by reference: U.S. Pat. No. 4,665,913 issued May 19, 1987 for "METHOD FOR OPTHALMOLOGICAL SURGERY;" U.S. Pat. No. 4,669,466 issued Jan. 2, 1987 for "METHOD AND APPARATUS FOR ANALYSIS AND CORRECTION OF ABNORMAL REFRACTIVE ERRORS OF THE EYE;" U.S. Pat. No. 4,732,148 issued Mar. 22, 1988 for "METHOD FOR PERFORMING OPHTHALMIC LASER SURGERY;" U.S. Pat. No. 4,770,172 issued Sep. 13, 1988 for "METHOD OF LASER-SCULPTURE OF THE OPTICALLY USED PORTION OF THE CORNEA;" U.S. Pat. No. 4,773,414 issued Sep. 27, 1988 for "METHOD OF LASER-SCULPTURE OF THE OPTICALLY USED PORTION OF THE CORNEA;" U.S. patent application Ser. No. 07/109,812 filed Oct. 16, 1987 for "LASER SURGERY METHOD AND APPARATUS;" and U.S. Pat. No. 5,163,934 issued Nov. 17, 1992 for "PHOTOREFRACTIVE KERATECTOMY."

A majority of patients develop various degrees of corneal haze following excimer photorefractive keratectomy (PRK) (Lohmann C, Gartry D, Kerr Muir M, et al. "Haze in Photorefractive Keratectomy: Its origins and consequences," Lasers and Light in Ophthal. 1991, 4, 15-34; Fante F E, Hanna K D, Waring G O, et al. "Wound healing after excimer laser keratomileusis (photorefractive keratectomy) in monkeys," Arch.

Ophthal. 1990, 108:665-675). Corneal haze typically peaks at two to four months and has been noted to increase with the degree of myopia corrected (e.g., 2+ stable haze defined according to the standard haze grading scale described by Fante et al., supra., occurs in 11% of patients with corrections greater than eight diopters. Such haze can lead to the loss of one or more lines of best corrected visual acuity after PRK. Corneal stromal remodeling influences the degree of corneal haze after PRK and is believed to be responsible for a reduction in the best possible corrected visual acuity, regression for refractive correction and poor predictability for the attempted correction.

The formation of the corneal haze after PRK is a result of laser corneal ablation and stromal wound healing. Despite significant advances made in understanding PRK technology (e.g., laser-tissue interaction, optical profiling of the laser beam, multi-zone multi-pass approaches and edge-smoothing techniques), characterization of biological aspects associated with PRK, such as wound healing, remains a significant limitation associated with PRK technology (Fante F E, Hanna K D, Waring G O, et cal., "Wound healing after excimer laser keratomileusis (photorefractive keratectomy) in monkeys," Arch. Ophthal. 1990, 108:665-675; Hanna K D, Pouliquen Y, Waring G O, et al., "Corneal stromal wound healing in rabbits after 193-nm excimer laser surface ablation," Arch. Ophthal. 1989, 107:895-901; Holm R J, Fouraker B D, Schanzlin D J. "A comparison of a face and tangential wide-area excimer surface ablation in rabbits," Arch. Ophthal. 1990, 108:876-881; Taylor D M, L'Esperance F A, Del Pera R A, et al., "Human excimer laser lamellar keratectomy, A clinical study," Opthal. 1989, 96:654-664; Marshal J, Trokel S, Rothery S, et al., "Photoablative reprofiling of the corneal using an excimer laser: photorefractive keratectomy," Lasers in Ophthal. 1986, 1:21-48; Tuft S, Marshall J, Rothery S. "Stromal remodeling following photorefractive keratectomy," Lasers Ophthal. 1987, 1:177-183). Treatments to reduce corneal haze after PRK have not been proven effective (O'Brat D, Lohmann C P, Klonos G, Corbett M C, Pollock W, Ker-Muir M G and Marshall J., "The effects of topical corticosteroids and plasmin inhibitors on refractive outcome, haze, and visual performance after photorefractive keratectomy," Ophthal. 1994, 101:1565-1574; Gartry, D S, Kerr Muir M G, and Marshall, J, "The effect of topical corticosteroids on refraction and corneal haze following excimer laser treatment of myopia: An update up a Prospective, randomized, double-masked study," Eye 1993, 7:584-590; Bergman R H, Spidelman A V, "The role of fibroblast inhibitors on corneal healing following photorefractive keratectomy with 193-nm excimer laser in rabbits," Ophthal Surg. 1994, 25(3):170-174; Talamo J H, Gollamudi S, Green W R, De La Cruz Z, Filatov V, Stark W J., "Modulation of corneal wound healing after excimer laser keratomileusis using topical mitomycin C and steroids," Arch. Ophthal. 1991, 109(8):1141-1146; Rieck P, David T, Hartman C, Renard G, Courtois Y and Pouliquen Y., "Basic fibroblast growth factor modulates corneal wound healing after excimer laser keratomileusis in rabbits," German J. Ophthal. 1994, 3:105-111; Morlet N, Gillies M C, Grouch R, Mallof A., "Effect of topical interferon-alpha 2b on corneal haze after excimer laser photorefractive keratectomy in rabbits," Refrac. Corneal Surg. 1993, 9(6):443-451; Filipec M, MaiPhan T, Zhao T-Z, Rice B A, Merchant A. and Foster C. Cornea, 1992, 11(6): 546-552; Mastubara M, Sasaki A, Ita S., "The effect of active vitamin D to the wound healing after excimer laser phototherapeutic keratectomy (PTK)," ARVO, 1996, 37(3): S198; Nuiizuma T, Ito S, Hayashi M Futemma M, Utsumi T, Ohashi K., "Cooling the cornea to prevent side effects of photorefractive keratectomy," Suppl. to J. Refract. & Corneal Surg. 1994, 10:S262-S266).

These various treatments for reducing corneal haze after excimer laser ablation have met with limited success. For example, the use of topical steroids has been found to be ineffective for the reduction of corneal haze. With regard to refractive outcome, though corticosteroids can maintain a hyperopic shift during their administration. However, the effect is reversed upon cessation of treatment. Consequently, there appears to be no justification for subjecting patients to long-term treatment with steroids for corneal haze in view of adverse side effects associated with steroidal treatments.

Other pharmacological treatments have also not been found to decrease post PRK haze. These treatments have included the use of plasmin inhibitors, fibroblast inhibitors, mitomycin, fibroblast growth factor, interferon-2b, cyclosporin A, active forms of vitamin D, as well as cooling of corneal surface (Rawe I M, Zabel R W, Tuft S J, Chen V and Meek K M., "A morphological study of rabbit corneas after laser keratectomy," Eye 1992, 6:637-642; Wu W C S, Stark W J and Green W R., "Corneal wound healing after 192-nm excimer laser keratectomy: Arch. Ophthalmol. 1991, 109:1426-1432).

SUMMARY OF THE INVENTION

In according to an aspect of the present invention, it is provided a method for reducing corneal scarring in a patient.

The method comprises intraocularly administering to an injured corneal tissue in a patient a composition comprising an effective amount of fibromodulin in a pharmaceutically acceptable formulation effective for reducing corneal scarring in the patient. The composition can be formulated into any formulation, optionally with a pharmaceutically acceptable carrier. In some embodiments, the formulation is an eye drop formulation, a lozenge.

In some embodiments, the composition can be formulated into a sustained release formulation to provide sustained release of fibromodulin. For example, the sustained release formulation can be a contact lens including the composition described herein.

In some embodiments, the composition can further comprises an agent other than fibromodulin. Such second agents can be, e.g., hyaluronic acid or a derivative thereof, or an anti-inflammatory agent.

The composition can have different concentration of fibromodulin. In some embodiments, the fibromodulin has a concentration of about 0.0001% by weight to about 5% by weight in the formulation. In some embodiments, the composition can further include a therapeutic agent.

The composition described herein can be used for reducing scarring in any injured corneal tissue. For example, the corneal tissue has been injured by a damaging condition such as trauma infection, corneal ulcers, chemical burns, ocular cicatricial pemphigoid, Stevens-Johnson syndrome, contact lens-induced keratopathy, or surgery.

In according to another aspect of the present invention, it is provided an eye composition for reducing scarring in an injured corneal tissue. The composition is as described above. In some embodiments, the composition can include a pharmaceutically acceptable carrier.

In according to a further aspect of the present invention, it is provided a kit. The kit comprises a composition that comprises an effective amount of fibromodulin, and an applicator for applying the composition to an eye of a patient.

DETAILED DESCRIPTION

The present invention pertains to a method for treating injured corneal tissue. The method includes contacting injured corneal tissue with a composition comprising fibromodulin, or a functional equivalent thereof. The contact lens includes an fibromodulin composition such that scarring of the injured corneal tissue is reduced or prevented. The composition can be used to prevent or reduce scarring in an injured corneal tissue.

The composition can have different concentration of fibromodulin or a functional equivalent thereof. In some embodiments, the composition can include from about 0.1 microgram to about 50 micrograms of fibromodulin or a functional equivalent thereof per one gram or one mL composition (0.0001% to about 5%). In some embodiments, the composition can have a second agent such as an anti-inflammatory agent, which is also referred as a therapeutic agent, as described in more detail below. In some embodiments, the second agent can be hyaluronic acid or a derivative thereof. A hyaluronic acid derivative can be a fragment of hyaluronic acid, a pharmaceutically acceptable salt of hyaluronic acid, or a compound that derived from hyaluronic acid.

The composition can be formulated into different formulation with a pharmaceutically acceptable carrier for application to eye. For example, the composition can be formulated into solid or semi-solid topical compositions such as lozenge, ointment, or gel. In some embodiments, the composition can be formulated into a liquid formulation such as a suspension or solution. Examples of liquid formulations include eye drop, for example.

In some embodiments, the formulation provides a sustained release of the fibromodulin. For example, the formulation can be included in a contact lens and released from the contact lens when a patient wears such a contact lens.

The composition can be used to prevent or reduce scarring in any corneal tissue that can result in scarring. For example, the corneal tissue can be injured by a damaging event such as: trauma infection, corneal ulcers, chemical burns, ocular cicatricial pemphigoid, Stevens-Johnson syndrome, contact lens-induced keratopathy, or surgery.

In some embodiments, the present invention provides a kit that comprises (a) a composition comprising an effective amount of fibromodulin or a functional equivalent thereof, and (b) an applicator for applying the formulation to an eye of a patient. The various embodiments of the composition are described above. The applicator is as described below.

Fibromodulin

The term "fibromodulin composition" is intended to mean a composition comprising an effective amount of fibromodulin or a proteoglycan protein other than fibromodulin, e.g., decorin, which is functionally equivalent to fibromodulin. Generally, the composition can include about 0.0001% to about 5% fibromodulin. For example, a topical administration may contain between about 50 pg/ml drug to about 50 micro gram/ml drug in a formulation which may be applied at bedtime or throughout the day.

Fibromodulin is a member of the family small leucine-rich proteoglycans (SLRPs). SLRPs are a family of proteins that are present in extracellular matrix and that share in common multiple repeats of a leucine-rich structural motif, flanked by cysteine residues. These proteins appear to interact in many cases with collagen, modifying the deposition and arrangement of collagen fibers in the extracellular matrix, and also with cells and with soluble growth factors. The interaction of SLRPs with cells and with growth factors like TGF-beta may affect the proliferation of cells in addition to modifying the extracellular environment. Postranslational modification of SLRPs with carbohydrates and sulfate-containing groups appears to modify the function of SLRPs. Changes in SLRP expression and modification in cornea, atherosclerotic plaque, joints, bone, tendons, and kidney may be associated with disease progression in those tissues. Decorin is one SLRP expressed throughout the body that stabilizes collagen fibrils and that also antagonizes the action of the cytokine TGF-beta, blocking cell cycle progression, and potentially playing a role in cancer and wound healing. The SLRP biglycan is expressed in bone and other connective tissues and genetic disruption of biglycan in mice causes low bone mass similar to osteoporosis.

The composition provided herein may optionally include a pharmaceutically acceptable carrier. Pharmaceutically acceptable carriers are well known in the art (Shai A, et al. Principles of preparation of medical and cosmetic products. *Handbook of Cosmetic Skin Care*. London: Martin Dunitz Ltd., pp. 19-31, 2001). A safe and effective amount of carrier can be from about 50% to about 99.99%, preferably from about 80% to about 99.9%, more preferably from about 90% to about 98%, and even more preferably from about 90% to about 95% of the composition.

The carrier can be in a wide variety of forms. For example, liquid carriers, or emulsion carriers, including, but not limited to, oil-in-water, water-in-oil, water-in-oil-in-water, and oil-in-water-in-silicone emulsions, are useful herein. A preferred liquid carrier is saline.

Emulsions according to the present invention generally contain a solution as described above and a lipid or oil. Lipids and oils may be derived from animals, plants, or petroleum and may be natural or synthetic (i.e., man-made). Representative emulsions also contain a humectant, such as glycerin. Emulsions will preferably further contain from about 0.01% to about 10%, more preferably from about 0.1% to about 5%, of an emulsifier, based on the weight of the carrier. Emulsifiers may be nonionic, anionic or cationic. Suitable emulsifiers are disclosed in, for example, U.S. Pat. No. 3,755,560 to Dickert et al.; U.S. Pat. No. 4,421,769 to Dixon et al.; and McCutcheon's Detergents and Emulsifiers, North American Edition, pages 317-324 (1986).

The emulsion may also contain an anti-foaming agent to minimize foaming upon application to the keratinous tissue. Anti-foaming agents include high molecular weight silicones and other materials well known in the art for such use.

Suitable emulsions may have a wide range of viscosities, depending on the desired product form. Exemplary low viscosity emulsions, which are representative, have a viscosity of about 50 centistokes or less, more preferably about 10 centistokes or less, still more preferably about 5 centistokes or less.

The compositions useful for the methods of the present invention are generally prepared by conventional methods such as are known in the art of making topical compositions. Such methods typically involve mixing of the ingredients in one or more steps to a relatively uniform state, with or without heating, cooling, application of vacuum, and the like.

Contact Lens Including Fibromodulin

The term "hyaluronic acid" is intended to include those polyanionic glycoaminoglycans affecting cellular activation and differentiation.

The term "contact lens" is art recognized and is intended to include those devices generally used for correction of visual acuity, for cosmetic purposes and for protection of the cornea, e.g., a device which does not correct for visual acuity. Contact lenses include those which are considered "hard", e.g. polymethylmethacrylate, which has excellent biocompatibility but has poor oxygen permeability, "rigid gas permeable", e.g., polysiliconemethacrylates which have excellent biocompatability and allow diffusion of oxygen through the polymeric structure and "soft", e.g., polyhydroxyethylmethacrylates which have excellent biocompatibility and also allow diffusion of oxygen through the polymeric structure by aqueous transport. Examples of materials used in contact lenses include polymethylmethacrylate, polysiliconeacrylates, polysiliconemethacrylates, polyfluoroacrylates, polyfluoromethacrylates, polyflurosiliconeacrylates, polysiliconemethacrylates, polymethacrylates, polyacrylates, polyurethanes, polysiliconeurethanes, or polyitaconates, and combinations thereof. These polymeric materials can also be crosslinked.

In one embodiment, a contact lens includes an fibromodulin composition in the form of a membrane or a film attached to the surface of the contact lens, preferably on the surface of the lens which is in contact with the injured corneal tissue. By "attached" in this context, reference is made not only to covalent bonding of amniotic membrane molecules to the contact lens surface but also to attractive interactions caused by such forces as hydrogen bonding, ionic bonding, bonding through Van der Waals forces and the like. For example, an fibromodulin composition can be covalently attached to the surface of a contact lens by the method taught in U.S. Pat. No. 4,973,493, the teachings of which are incorporated herein by reference.

The term "membrane" is art recognized and is intended to include those materials having a pore structure within the biological matrix. In general, a membrane has a pore size of between about 0.02 µm to about 2 µm and a thickness of between about 0.001 mm and about 0.1 mm. Preferably, amniotic membranes useful in this invention consist of three layers; the epithelium, basement membrane and stroma, the combination of which having a total thickness of between about 50 µm to about 100 µm.

The term "film" is also art recognized and is intended to include a continuous coating of the contact lens surface substantially devoid of pore structure throughout the film matrix. In general, the film has a thickness of between about 0.001 mm and about 0.1 mm. Preferably, the film has thickness of about 0.05 to about 0.5 mm.

Alternatively, the contact lens surface can have an fibromodulin composition which is a discontinuous layer. By the term "discontinuous" it is meant that discrete particles are attached to the contact lens surface. Preferably, at least about 50 percent of the contact lens surface area, which is in contact with the injured corneal tissue, has fibromodulin composition particulates. More preferably, at least about 75 percent of the contact lens surface has fibromodulin composition particulates, more preferably at least about 90 percent of the contact lens surface has particulates. In a most preferred embodiment, between about 95 and 99 percent of the contact lens surface area, which is in contact with the injured corneal tissue, has fibromodulin composition particulates.

The fibromodulin composition particulates range in size from between about 0.2 µm to about 10 µm. Preferably, the particulates range in size from between about 0.5 µm to about 5 µm. The particulates can be of varying sizes and dimensions, e.g. round, oblong, disc like. Furthermore, the particulates can be porous.

In another embodiment, the contact lens which is in contact with injured corneal tissue includes an fibromodulin composition which is entrapped within the contact lens. Therefore, the necessary tissue growth factors diffuse from within the contact lens, thereby stimulating healing of the injured corneal tissue.

In a preferred embodiment, the contact lenses of the invention which have either an amniotic membrane, film, or particulates attached to the surface of the contact lens, or which have the fibromodulin composition entrapped within the contact lens are periodically treated with a solution including an fibromodulin composition. For example, daily treatment of the contact lenses with a solution including an fibromodulin composition provides for incorporation of additional growth and tissue repair factors in the membrane, film, particulate or within the contact lens. The contact lens having the fibromodulin composition can be soaked in the solution for between about 1 to 12 hours; often overnight while the individual is sleeping.

Conditioning of the contact lens with solutions which contain fibromodulin compositions can be utilized to replenish or to increase growth and tissue repair factors as required. Typical concentrations of the fibromodulin composition in the solution are between about 2 percent and about 20 percent, preferably between about 5 percent and about 10 percent. Further, the solution can also include antibiotics such as amino glycosides, preferably tobramycin (O-3-amino-3-deoxy-.alpha.-D-glycopyranosyl-(1.fwdarw.4)-O-[2,6-diamino-2, 3,6-trideoxy-.alpha.-D-ribo-hexopyranosyl-(1.fwdarw.6)]-2-deoxy-L-streptami ne) to prevent infection during corneal tissue healing. Typical concentrations of the antibiotic(s) is in a range of between about 2 percent and about 20 percent, preferably between about 5 percent and about 10 percent.

It will be appreciated by one skilled in the art that art-known methods of testing the parameters of treatment with the amniotic fluid-treated contact lens of the invention may be utilized to determine its most efficacious use in the treatment of different corneal tissue injuries.

It will also be appreciated by one skilled in the art that the methods and the contact lens packages of the invention may also be efficaciously used to prevent scarring in regions of the eye other than the cornea which have sustained injury, or in tissues adjacent to the eye in the ocular cavity. Such regions may include, but are not limited to, the iris or the retina. Although the contact lens primarily is in contact only with the cornea itself, other regions of the eye may be exposed to one or more of the components of the fibromodulin composition with which the contact lens is treated. For example, components of the fibromodulin composition may diffuse through the cornea and into surrounding ocular tissues, may enter capillaries and be widely distributed through the eye, or may be solubilized by tears and distributed to surrounding tissues.

Injury to Corneal Tissue

The mechanism leading to corneal injury can vary from tissue to tissue. Injury to corneal tissue impairs the functions of eye, which follows the general principles of physics. Photoablated corneal tissue serves as a useful model of corneal tissue injury in general, and so will also serve as a good model for the explication of the uses and methods of the invention.

Photoablation of corneal tissue can be accomplished by excimer photorefractive keratectomy (PRK) for refractive correction of myopia, hyperopia, presbyopia and astigmatism. Photoablation of corneal tissue can also be accomplished by phototherapeutic keratectomy (PTK) for removal of anterior corneal opacities such as scarring after trauma or infection, or corneal dystrophies. A common problem associated with both PRK and PTK is the development of corneal haze/scarring of the photoablated corneal tissue. Corneal haze is the result of scarring after laser corneal ablation and is responsible for regression of the refractive correction and loss of best-corrected visual acuity after photoablative treatment.

The present invention also pertains to a method of conditioning a contact lens for treatment of injured corneal tissue. The method includes contacting the contact lens with an fibromodulin composition whereby the fibromodulin composition is deposited within the contact lens or on the surface of the contact lens. Suitable fibromodulin compositions include extracts from amniotic tissue and placental components.

The language "photoablated corneal tissue" is intended to cover that area of the cornea subjected to photoablative treatment, e.g. PRK or PTK, for reshaping of the surface of the cornea. Such photoablative treatment can be used for the correction of astigmatism myopia, hyperopia, presbyopia and for treating corneal pathology such as known to a person skilled in the art. Photoablation, generally, refers to the use of an intense beam of ultraviolet or infrared light having sufficient energy to cut into or through corneal tissue. Suitable sources of light include lasers, such as excimer lasers, infrared lasers, free-electron lasers with a wide range of ablative energy. The applied radiation is controlled in a manner such that desired reshaping of the cornea is obtained. The desired amount of correction is determined clinically based on refraction and a computer controlled laser delivery system to deliver the precise number of laser shots at predetermined locations on the cornea. The optical profile of the resulting corneal contours enables refocusing of images on the retina to achieve clear vision. For example, photorefractive keratectomy can be performed with a 193-µm excimer laser under topical anesthesia. A 193-µm excimer laser produces a beam with an energy of 180 mJ/cm$^2$ at a firing rate of 10 hertz. Each pulse ablates to a 0.25-µm depth of the corneal stroma. Commercial apparatus for photoablative surgery are art recognized and include for example Summit Technology's EXCIMED UV200 (Waltham, Mass.) and the VisX STAR (Santa Clara, Calif.).

The term "injured corneal tissue" is intended to include corneal tissue which has been damaged as a result of physical trauma, infection, or a disease state. Trauma to the cornea can be a result of, but is not limited to, chemical burns, contact-lens-induced keratopathy, photoablation, and lacerations from external sources. Infections which are known to be damaging to corneal tissue include those of bacterial, viral, and fungal origin, particularly herpes virus infection. Disease states resulting in damage to corneal tissue include, but are not limited to ocular cicatricial pemphigoid, Stevens-Johnson syndrome, and persistent corneal ulcers. A model example of corneal tissue injury is the damage sustained by photoablation, due to the extensive research which has been performed on this type of corneal damage, and also to the controlled circumstances under which the injury takes place. Photoablated corneal tissue, then, provides a useful model system for the uses and methods of the invention.

The contents of all references, pending patent applications and published patent applications, cited throughout this application are hereby incorporated by reference.

Liquid Formulation

In some embodiments, the present invention provides a liquid formulation effective for reducing corneal scarring topically comprising an aqueous solution or suspension comprising fibromodulin or a functional equivalent thereof, wherein the composition has a pH of about 4.0 to about 8.0, preferably about 5.0 to about 6.8, and at least some of the agent is maintained as a reservoir established in suspension at the pH of the formulation. The amount established in suspension may vary depending on therapeutic needs but it will be at least an amount sufficient to have a therapeutic effect on the eye upon delayed release from the suspension over a period of time. A sufficient amount of agent will also be present in solution to have an immediate therapeutic effect upon topical ophthalmic application. Typically, about 80% to about 90% of the total agent contained in the mixture will be in suspension, but this may vary depending on how much of the agent is desired for delivery and the duration of delivery desired. The amount of therapeutic agent in suspension may, for instance, range from about 70% to about 99% or about 10% to about 99% by weight of the total amount of agent contained in the mixture. The compositions will not, however, have 100% of the agent in suspension. Some amount will be in solution to provide the immediate therapeutic effect. Compositions of the present invention may have a pH of about 4 to about 8 depending on the solubility characteristics of the agent. In a preferred embodiment where diclofenac is the therapeutic agent, a preferred pH range is about 5.0 to about 6.8. The concentration of the agent and the pH of the composition will be selected to ensure that a sufficient amount of the therapeutic agent is in suspension to provide a therapeutic effect upon delayed deliver. In this way, the portion of the agent in solution is immediately available for therapeutic effect while the portion in suspension serves as a reservoir and is released slowly over time.

In some embodiments, the formulation is a suspension. Formulating the composition as a suspension rather than as a solution inhibits immediate contact between the drug and tissues of the eye and in that way reduces the stinging and burning sensation experienced when a solution of such drugs places all of the drug in immediate contact with the ocular tissues.

The various agents have different solubilities at a given pH. These differences in solubility are known or can be ascertained with techniques familiar to those of ordinary skill in the art. The amount of non-steroidal anti-inflammatory agent in suspension for use in the present compositions will therefore vary depending, for example, on the specific agent or drug chosen, the dosage required, the desired release profile (the degree of sustained release), the condition for which the drug is administered and the pH of the composition. Generally, however, it is preferred to have formulations with about 70%-99% of the total agent in suspension although other amounts may be used (such as 10%-99%), so long as at least some of the agent is in suspension; that is an amount sufficient to have a therapeutic effect during delayed release. As previously explained, a therapeutic amount must also be in solution. The total amount of therapeutic agent, or drug, is present in the composition in an amount effective to treat the selected target condition. Generally, the concentration of agent will be about 0.001% (10 ppm) to about 5.0% by weight of the composition. In some embodiments, the agent is about 0.005 to about 3.0% by weight of the composition or about 0.1 to about 1.0% by weight of the composition. These same ranges of drug concentrations are believed to be appropriate for treating a wide range of conditions that require therapeutic treatment.

The pH and concentration of the agent in the formulation are selected to provide sufficient drug in solution to begin effective therapeutic treatment but at least some in suspension to serve as a depot for the agent which delays release of that agent over time. The pH of the aqueous mixture may be about 4.0 to about 8.0 and preferably, about 5.0 to about 6.8, but at a level sufficient to establish the desired suspension amount of the agent.

Preferably, in one embodiment, the composition can be formulated as an aqueous suspension. The composition may contain water soluble polymers or water insoluble polymers as the suspending agent. Examples of such soluble polymers are cellulosic polymers like hydroxypropyl methylcellulose. Water insoluble polymers are preferably crosslinked carboxy-vinyl polymers. It is important to note, however, that the present invention requires the agent to be in suspension without reference to whether the polymer is or is not in suspension.

A preferred form of the invention incorporates insoluble polymers to provide a gel or liquid drops which release the drug over time. Preferably, the polymer is about 0.1 to about 6.5%, more preferably about 1.0 to about 1.3% by weight based on the total weight of the suspension of a crosslinked carboxy-containing polymer. Suitable carboxy-containing polymers for use in the present invention and method for making them are described in U.S. Pat. No. 5,192,535 to Davis et al. which is hereby incorporated by reference and relied upon. These polymer carriers include lightly crosslinked carboxy-containing polymers (such as polycarbophil, or Carbopols®), dextran, cellulose derivatives, polyethylene glycol 400 and other polymeric demulcents such as polyvinylpyrrolidone, polysaccaride gels and Gelrite®. A carboxy-containing polymer system known by the tradename DuraSite®, containing polycarbophil, is a sustained release topical ophthalmic delivery system that releases the drug at a controlled rate, may also be used.

Aqueous mixtures of this invention may also contain amounts of suspended lightly crosslinked polymer particles ranging from about 0.1% to about 6.5% by weight, and preferably from about 0.5% to about 4.5% by weight, based on the total weight of the aqueous suspension. They will preferably be prepared using pure, sterile water, preferably deionized or distilled, having no physiologically or ophthalmologically harmful constituents, and will be adjusted to a pH of from about 4.0 to about 6.8, and preferably from about 5.5 to about 6.5, using any physiologically and ophthalmologically acceptable pH adjusting acids, bases or buffers, e.g., acids such as acetic, boric, citric, lactic, phosphoric, hydrochloric, or the like, bases such as sodium hydroxide, sodium phosphate, sodium borate, sodium citrate, sodium acetate, sodium lactate, THAM (trishydroxymethylaminomethane), or the like and salts and buffers such as citrate/dextrose, sodium bicarbonate, ammonium chloride and mixtures of the aforementioned acids and bases.

When formulating the aqueous suspensions, their osmotic pressure (.pi.) may be adjusted to from about 10 milliosmolar (mOsM) to about 400 mOsM, using appropriate amounts of physiologically and ophthalmologically acceptable salts. Sodium chloride is preferred to approximate physiologic fluid, and amounts of sodium chloride ranging from about 0.01% to about 1% by weight, and preferably from about 0.05% to about 0.45% by weight, based on the total weight of the aqueous suspension, will give osmolalities within the above-stated ranges. Equivalent amounts of one or more salts made up of cations such as potassium, ammonium and the like and anions such as chloride, citrate, ascorbate, borate, phosphate, bicarbonate, sulfate, thiosulfate, bisulfate, sodium bisulfate, ammonium sulfate, and the like can also be used in addition to or instead of sodium chloride to achieve osmolalities within the above-stated ranges. Sugars like mannitol, dextrose, glucose or other polyols may be added to adjust osmolarity.

The amounts of insoluble lightly crosslinked polymer particles, the pH, and the osmotic pressure chosen from within the above-stated ranges will be correlated with each other and with the degree of crosslinking to give aqueous suspensions having viscosities ranging from about 500 to about 100,000 centipoise, and preferably from about 5,000 to about 30,000 or about 5,000 to about 20,000 centipoise, as measured at room temperature (about 25.degree. C.) using a Brookfield Digital LVT Viscometer equipped with a number 25 spindle and a 13R small sample adapter at 12 rpm. Formulations of the present invention should have a viscosity that is suited for the selected route of administration. Viscosity up to about 30,000=drop. About 30,000 to about 100,000 centipoise is an advantageous viscosity range for ophthalmic administration in ribbon form.

When water soluble polymers are used, such as hydroxypropyl methylcellulose, the viscosity will typically be about 10 to about 400 centipoises, more typically about 10 to about 200 centipoises or about 10 to about 25 centipoises.

The composition of the present invention will ordinarily contain surfactants and, if desired, adjuvants, including additional medicaments, buffers, antioxidants, tonicity adjusters, preservatives, thickeners or viscosity modifiers, and the like. Additives in the formulation may desirably include sodium chloride, EDTA (disodium edetate), and/or BAK (benzalkonium chloride) or sorbic acid.

In some embodiments, the composition can include ophthalmic medicaments which are drugs intended to treat therapeutically conditions of the eye itself or the tissue surrounding the eye and drugs administered via the ophthalmic route to treat therapeutically a local condition other than that involving the eye. The ophthalmic medicaments will typically be incorporated in the topical delivery systems of this invention in therapeutically active amounts comparable to amounts administered in other dosage forms, usually in amounts ranging from about 0.001% to about 5% by weight, and preferably from about 0.1% to about 1% by weight, based on the total weight of the formulation. Thus, for example, about 0.1% to about 1.0% by weight of the ophthalmic medicaments can be administered to the eye in this manner.

The viscous gels that result from fluid eyedrops delivered by means of the aqueous suspensions of this invention typically have residence times in the eye ranging from about 2 to about 12 hours, e.g., from about 3 to about 6 hours. The agents contained in these drug delivery systems will be released from the gels at rates that depend on such factors as the drug itself and its physical form, the extent of drug loading and the pH of the system, as well as on any drug delivery adjuvants, such as ion exchange resins compatible with the ocular surface, which may also be present. Preferably, the aqueous suspensions provide sustained concentration of the non-steroidal anti-inflammatory agent of between $10^{-8}$ and $10^{-4}$ M, and more preferably between $10^{-7}$ and $10^{-5}$ M, in the aqueous or treated tissue of the eye for at least two hours, preferably at least three hours.

Ophthalmic suspensions of the present invention may be formulated so that they retain the same or substantially the same viscosity in the eye that they had prior to administration to the eye. Alternatively, ophthalmic suspensions of the present invention may be formulated so that there is increased gelation upon contact with tear fluid. For instance, when a formulation containing DuraSite® is administered to the eye at a lower pH, the DuraSite® system swells upon contact with tears. This gelation or increase in gelation leads to entrapment of the suspended drug particles, thereby extending the residence time of the composition in the eye. The drug is released slowly as the suspended particles dissolve over time as the solubility of the drug is higher in the tear fluid. All these events eventually lead to increased patient comfort, increase in the time the drug is in contact with the eye tissues, thereby increasing the extent of drug absorption and duration of action of the formulation in the eye.

In general, ophthalmic formulations suitable for topical ophthalmic administration may be formulated and administered in accordance with techniques familiar to persons skilled in the art. The finished formulations are preferably stored in opaque or brown containers to protect them from light exposure, and under an inert atmosphere. These aqueous suspensions can be packaged in preservative-free, single-dose non-reclosable containers. This permits a single dose of the medicament to be delivered to the eye as a drop or ribbon, with the container then being discarded after use. Such containers eliminate the potential for preservative-related irritation and sensitization of the corneal epithelium, as has been observed to occur particularly from ophthalmic medicaments containing mercurial preservatives. Multiple dose containers can also be used, if desired, particularly since the relatively low viscosities of the aqueous suspensions of this invention permit constant, accurate dosages to be administered dropwise to the eye as many times each day as necessary. In those suspensions where preservatives are to be included, suitable preservatives are chlorobutanol, polyquat, benzalkonium chloride, cetyl bromide, sorbic acid and the like.

Other Agents

In some embodiments, the composition described herein may include at least one agent other than fibromodulin or a functional equivalent thereof. Such other agents include, but are not limited to, steroidal or non-steroidal anti-inflammatory agents, analgesic, and antibacterial agents.

Non-steroidal anti-inflammatory agents as used herein are intended to mean any non-narcotic analgesic/nonsteroidal anti-inflammatory compound useful as a cyclooxygenase inhibitor. Preferably the non-steroidal anti-inflammatory agent is one or more of to the following: aspirin, benoxaprofen, benzofenac, bucloxic acid, butibufen, carprofen, cicloprofen, cinmetacin, clidanac, clopirac, diclofenac, etodolac, fenbufen, fenclofenac, fenclorac, fenoprofen, fentiazac, flunoxaprofen, furaprofen, flurbiprofen, furobufen, furofenac, ibuprofen, ibufenac, indomethacin, indoprofen, isoxepac, ketroprofen, lactorolac, lonazolac, metiazinic, miroprofen, naproxen, oxaprozin, oxepinac, phenacetin, pirprofen, pirazolac, protizinic acid, sulindac, suprofen, tiaprofenic acid, tolmetin, and zomepirac. Preferably, the agent is selected from the group consisting of diclofenac, suprofen, and flurbiprofen sodium and mixtures thereof. More preferably, the non-steroidal anti-inflammatory agent is diclofenac sodium.

A Kit

In some embodiments, it is provided a kit for eye. The kit comprises a composition that comprises an effective amount of fibromodulin as defined in the various embodiments above, and an applicator for applying the composition to an eye of a patient.

Applicators for applying a formulation to eye are common and commercially available. Any applicator suitable for delivering an eye formulation can be used for delivering a composition described herein. In some embodiments, the applicator can include an indicator such as one described in U.S. Pat. No. 5,382,243, the teaching of which is incorporated herein by reference. In other embodiments, the applicator can include an application aid such as a pressure aid as described in U.S. Pat. No. 5,467,147, the teaching of which is incorporated herein by reference.

Those skilled in the art will know, or be able to ascertain, using no more than routine experimentation, many equivalents to the specific embodiments of the invention described herein. These and all other equivalents are intended to be encompassed by the following claims.

What is claimed is:
1. An eye formulation, comprising:
an effective amount of fibromodulin effective for reducing scarring in an injured corneal tissue of a patient, a second agent, and a pharmaceutically acceptable carrier,
wherein the formulation is suitable for topical application to an eye of the patient,
wherein the formulation is an aqueous suspension, wherein the effective amount is about 0.0001% to about 5% fibromodulin by weight, and wherein the formulation has a viscosity such that the formulation has a residence time in the eye from about 2 to 12 hrs.

2. The eye formulation of claim 1, which is an eye drop.

3. The eye formulation of claim 1, which provides sustained release of the fibromodulin.

4. The eye formulation of claim 1, wherein the second agent is a therapeutic agent.

5. The eye formulation of claim 1, wherein the second agent is an anti-inflammatory agent, an antibacterial agent, or an analgesic agent.

6. The eye formulation of claim 1, wherein the carrier is an aqueous carrier.

7. The eye formulation of claim 6, wherein the formulation is a liquid suspension having a pH from about 5 to about 8.

8. The eye formulation of claim 1, wherein the corneal tissue has been injured by a damaging condition selected from the group consisting of: trauma infection, corneal ulcers, chemical burns, ocular cicatricial pemphigoid, Stevens-Johnson syndrome, contact lens-induced keratopathy, and surgery.

9. The eye formulation of claim 1, having an osmotic pressure from about 10 milliosmolar (mOsM) to about 400 mOsM.

10. The eye formulation of claim 1, having a viscosity selected from the group consisting of about 10 to about 25 centipoises, about 10 to about 200 centipoises, about 10 to about 400 centipoises, about 5,000 to about 30,000 centipoise, about 5,000 to about 20,000 centipoise, and about 500 to about 100,000 centipoise.

11. A contact lens comprising an eye formulation according to claim 1.

12. A kit, comprising the eye formulation of claim 1 and an applicator for applying the formulation to an eye of a patient.

13. A method for reducing corneal scarring in a patient comprising:

intraocularly administering to an injured corneal tissue in the patient an eye formulation of a composition comprising:

an effective amount of fibromodulin for reducing scarring in the injured corneal tissue of the patient, hyaluronic acid and a pharmaceutically acceptable carrier, wherein the eye formulation is an aqueous suspension and is suitable for topical application to an eye of the patient, wherein the effective amount comprises about 0.0001% to about 5% fibromodulin by weight, and wherein the formulation has a viscosity such that the formulation has a residence time in the eye from about 2 to 12 hrs.

14. The method of claim 13, wherein the formulation is an eye drop formulation.

15. The method of claim 13, wherein the formulation is a semi-sold topical formulation.

16. The method of claim 13, wherein the formulation is a liquid formulation.

17. The method of claim 13, wherein the formulation is a liquid suspension having a pH from about 5 to about 8.

18. The method of claim 13, wherein the formulation provides a sustained release of the fibromodulin.

19. The method of claim 18, wherein the formulation is included in a contact lens.

20. The method of claim 13, wherein the corneal tissue has been injured by a damaging condition selected from the group consisting of: trauma infection, corneal ulcers, chemical burns, ocular cicatricial pemphigoid, Stevens-Johnson syndrome, contact lens-induced keratopathy, and surgery.

* * * * *